US009759720B2

(12) United States Patent
Björck et al.

(10) Patent No.: US 9,759,720 B2
(45) Date of Patent: Sep. 12, 2017

(54) DIAGNOSTIC METHOD FOR BACTERIAL MENINGITIS

(75) Inventors: Lars Björck, Lund (SE); Bertil Christensson, Lund (SE); Heiko Herwald, Veberöd (SE); Adam Linder, Lund (SE); Per Åkesson, Lund (SE)

(73) Assignee: Hansa Medical AB, Lund (SE)

( * ) Notice: Subject to any disclaimer, the term of this patent is extended or adjusted under 35 U.S.C. 154(b) by 405 days.

(21) Appl. No.: 13/825,528

(22) PCT Filed: Sep. 23, 2011

(86) PCT No.: PCT/EP2011/066611
§ 371 (c)(1),
(2), (4) Date: Dec. 3, 2013

(87) PCT Pub. No.: WO2012/038541
PCT Pub. Date: Mar. 29, 2012

(65) Prior Publication Data
US 2014/0080754 A1     Mar. 20, 2014

(30) Foreign Application Priority Data
Sep. 24, 2010   (GB) .................................. 1016161.0

(51) Int. Cl.
*G01N 33/569* (2006.01)
*G01N 33/68* (2006.01)

(52) U.S. Cl.
CPC . *G01N 33/56911* (2013.01); *G01N 33/56944* (2013.01); *G01N 33/6893* (2013.01); *G01N 2333/4721* (2013.01)

(58) Field of Classification Search
CPC ................................ C07K 9/008; A61K 38/00
See application file for complete search history.

(56) References Cited

U.S. PATENT DOCUMENTS

| | | | |
|---|---|---|---|
| 5,420,016 A | 5/1995 | Boguslaski et al. | |
| 5,627,262 A | 5/1997 | Pereira | |
| 5,962,241 A | 10/1999 | Ax et al. | |
| 5,976,536 A * | 11/1999 | Stephens et al. | 424/184.1 |
| 6,303,321 B1 | 10/2001 | Tracey et al. | |
| 7,655,480 B2 | 2/2010 | Pereira | |
| 7,767,395 B2 | 8/2010 | Garrett et al. | |
| 8,518,648 B2 * | 8/2013 | Bjorck ............... | G01N 33/6893 |
| | | | 435/7.1 |
| 2003/0170745 A1 | 9/2003 | Pereira | |
| 2004/0197930 A1 | 10/2004 | Rosenfeld et al. | |
| 2005/0196817 A1 | 9/2005 | Kingsmore et al. | |
| 2006/0173162 A1 | 8/2006 | Djurup | |
| 2007/0092911 A1 | 4/2007 | Buechler et al. | |
| 2007/0110804 A1 | 5/2007 | Royer | |
| 2007/0166768 A1 | 7/2007 | Pereira | |
| 2007/0269437 A1 | 11/2007 | Djurup et al. | |
| 2009/0221021 A1 | 9/2009 | Chalumeau et al. | |
| 2014/0080925 A1 | 3/2014 | Björck et al. | |
| 2014/0187503 A1 | 7/2014 | Björck et al. | |

FOREIGN PATENT DOCUMENTS

| | | |
|---|---|---|
| WO | WO 95/28949 | 11/1995 |
| WO | WO 98/32390 A1 | 7/1998 |
| WO | WO 00/47104 | 8/2000 |
| WO | WO 03/076459 A1 | 9/2003 |
| WO | WO 2004/016653 A2 | 2/2004 |
| WO | WO 2004/088324 A2 | 10/2004 |
| WO | WO 2004/112713 A2 | 12/2004 |
| WO | WO 2005/028512 A1 | 3/2005 |
| WO | WO 2007/045873 A2 | 4/2007 |
| WO | WO 2007/068830 A1 | 6/2007 |
| WO | WO 2008/151808 A1 | 12/2008 |
| WO | WO 2012/038541 A1 | 3/2012 |
| WO | WO 2012/107450 A1 | 8/2012 |

OTHER PUBLICATIONS

By E. Behling-Kelly (Infection and Immunity, Sep. 2006, p. 5311-5318 vol. 74, No. 90019-9567/06/$08.00_0 doi:10.1128/IAI.00614-06).*
UK IPO Search Report from GB1016161.0 dated Apr. 15, 2011.
Beran et al., 2010, "Heparin-binding Protein as a Biomarker of Circulatory Failure during Severe Infections: A Report of Three Cases," *Scandinavian Journal of Infectious Diseases* 42:634-636.
Linder et al., 2009, "Heparin-binding Protein: An Early Marker of Circulatory Failure in Sepsis," *Clinical Infectious Diseases* 49(7):1044-1050.
Linder et al., 2010, "Roles of Heparin-Binding Protein in Bacterial Infections," *Journal of Innate Immunity* 2:431-438.
Linder et al., 2011, "Heparin-binding Protein: A Diagnostic Marker of Acute Bacterial Meningitis," *Critical Care Medicine* 39(4):812-817.
Mariscalco et al., 2011, "Heparin-binding Protein: Another Neutrophil Granule Protein . . . Another New Biomarker?," *Critical Care Medicine* 39(4):910-911.

(Continued)

*Primary Examiner* — Marcela M Cordero Garcia
*Assistant Examiner* — Catherine Mader
(74) *Attorney, Agent, or Firm* — Dechert LLP

(57) ABSTRACT

It has been demonstrated that the level of HBP increases in individuals that have bacterial meningitis. Accordingly, the level of HBP in an individual can be used to determine whether or not an individual has bacterial meningitis.

15 Claims, 3 Drawing Sheets

(56) References Cited

OTHER PUBLICATIONS

Tapper et al., 2002, "Secretion of Heparin-binding Protein from Human Neutrophils is determined by its Localization in Azurophilic Granules and Secretory Vesicles," *Blood, American Society of Hematology* 99(5):1785-1793.
PCT International Search Report from PCT/EP2011/066611 date mailed Sep. 1, 2012.
Serruto et al., 2010, "Neisseria Meningitidis GNA2132, A Heparin-Binding Protein that Induces Protective Immunity in Human," *Proc. Natl. Acad. Sci USA*. 107(8):3770-3775.
Yoshida et al., 2008, "Expression of the Heparin-Binding Growth Factor Midkine in the Cerebrospinal of Patients with Neurological Disorders," *Internal Medicine* 47(2):83-89.
Bochud et al., (2004) "Antimicrobial therapy for patients with severe sepsis and septic shock: An evidence-based review," *Crit Care Med*. 32(11 Suppl.):S495-S512.
Bossink et al., (1999) "The Clinical Host Response to Microbial Infection in Medical Patients with Fever," *Chest* 116(2):380-390.
Claessens (2007) "Diagnosis and Treatment of Severe Sepsis," *Critical Care* 11(Suppl 5):1-8.
Gautam et al., (2001) "Heparin-Binding Protein (HBP/CAP37): A Missing Link in Neutrophil-Evoked Alteration of Vascular Permeability," *Nat Med*. 7(10):1123-1127.
Kahn et al., (2002) "Contact-System Activation in Children with Vasculitis" *National Library of Medicine* Abstract No. 12241658.
Kjölvmark et al., (2012) "Elevated Urine Levels of Heparin-Binding Protein in Children with Urinary Tract Infection," *Pediatr Nephrol* 27(8):1301-1308.
Lennard et al., (1982) "Implications of Leukocytosis and Fever at Conclusion of Antibiotic Therapy for Intra-abdominal Sepsis," *Ann Surg*. 195(1):19-24.
O'Grady et al., (1999) "Detection of Macrophage Inflammatory protein (MIP)-1α and MIP-1β during Experimental Endotoxemia and Human Sepsis," *J Infect Dis*. 179:136-141.
Weiss et al., (2003) "Transient Leukocytosis, Granulocyte Colony-Stimulating Factor Plasma Concentrations, and Apoptosis Determined by Binding of Annexin V by Peripheral Leukocytes in Patients with Severe Sepsis," *Ann N.Y Acad. Sci*. 1010:742-747.
Wolpe et al., (1989) "Macrophage Inflammatory proteins 1 and 2: Members of a Novel Superfamily of Cytokines," *FASEB J*. 3:2565-2573.
Woodford et al., (2011) "Diagnosis and Management of Urinary Infections in Older People," *Clinical Medicine, Royal College of Physicians* 11(1):80-83.
Peltola et al. , (2006) "Comparison of total white blood cell count and serum C-reactive protein levels in confirmed bacterial and viral infections," *J Pediatr*. 149(5):721-724.
Mussap et al., (2006) "Laboratory Investigation for the Early Diagnosis and Monitoring of Neonatal Urinary Tract Infections: the Present Situation and Future Perspectives," *Journal of Chemotherapy* 18(3):9-13.
O'Grady et al., (1999) "Detection of Macrophage Inflammatory protein (MIP)-1α and MIP-1β during Experimental Endotoxemia and Human Sepsis," *J Infect Dis*. 179:136-141.
PCT International Search Report from PCT/EP2008/004743 dated Nov. 11, 2008.
PCT International Preliminary Report on Patentability for PCT/EP2008/004743, dated Nov. 8, 2009.
PCT International Search Report from PCT/EP2012/052059 dated Dec. 4, 2012.
Pereira et al., (1989) "Quantitation of a cationic antimicrobial granule protein of human polymorphonuclear leukocytes by Elisa," *J Immunological Methods* 117:115-120.
Reining et al., (2001) *Nat Med*. 7:S87.
Soehnlein et al., (2005) "Neutrophil-derived heparin-binding protein (HBP/CAP37) deposited on endothelium enhances monocyte arrest under flow conditions," *J Immunol*. 174(10):6399-405.
UK Intellectual Property Office Search Report from GB0711327.7 dated Aug. 22, 2007.
Wang et al., (2006) "Specific Cleavage of Insulin-like Growth Factor-Binding Protein-1 by a Novel Protease Activity," *Cellular and Molecular Life Sciences* 63(19-20):2405-2414.
Weiss et al., (2003)"Transient Leukocytosis, Granulocyte Colony-Stimulating Factor Plasma Concentrations, and Apoptosis Determined by Binding of Annexin V by Peripheral Leukocytes in Patients with Severe Sepsis," *Ann N. Y Acad. Sci*. 1010:742-747.

\* cited by examiner

DIAGNOSTIC METHOD FOR BACTERIAL MENINGITIS

CROSS REFERENCE TO RELATED APPLICATIONS

This is the §371 U.S. national stage of International Application No. PCT/EP2011/066611, filed Sep. 23, 2011, which claims the benefit of United Kingdom application no. 1016161.0, filed Sep. 24, 2010, the disclosures of which are incorporated herein by reference in their entireties.

FIELD OF THE INVENTION

The invention relates to the diagnosis and treatment of bacterial meningitis.

BACKGROUND OF THE INVENTION

Bacterial meningitis is a life-threatening disease. In adults, *Streptoccocus pneumoniae* and *Neisseria meningitidis* are the predominant agents, with an overall fatality rate of approximately 30% and 10%, respectively. Viral meningitis and encephalitis is also life-threatening. Although the most common causative agent (enterovirus) presents relatively rarely with neurological complications, Herpes simplex-1 (HSV-1) meningoencephalitis has >70% mortality if untreated. Early treatment improves prognosis in all forms of meningitis and encephalitis, and therefore early diagnosis is vital.

Diagnosis and treatment remain a major challenge, mainly due to the often difficult distinction of acute bacterial meningitis from viral CNS infection or neuroborreloiosis at presentation. Conventional clinical and laboratory variables such as White Blood Cell (WBC) count, or levels of lactate, protein, glucose, or plasma C-reactive protein (CRP), typically measured in the cerebrospinal fluid (CSF), are often not discriminative enough in the early phase of the disease. Final diagnosis requires a blood or CSF culture positive for bacterial infection, or positive identification of bacteria in the CSF following, for example, Gram-staining. A positive result in one of these assays is generally taken to be proof of a bacterial origin is proven and further tests are not necessary. However, these tests have an overall sensitivity of only 60% to 90%. Also, many patients receive antibiotics prior to lumbar puncture, reducing the chance of a definitive result from CSF culture or Gram-staining. Culture in particular is also time-consuming, leading to a delay in diagnosis. As a result of these factors, patients suspected of having meningitis are typically given a default treatment of broad-spectrum antibiotics and antiviral therapy, pending final diagnosis.

A reliable biological or clinical marker to determine as early as possible whether or not an individual has bacterial meningitis is needed.

SUMMARY OF THE INVENTION

Heparin-binding protein (HBP, CAP37, Azurocidin) is a glycosylated, single chain, positively charged 37 kDa inactive serine protease homologue exhibiting 44% sequence identity with human neutrophil elastase. The three dimensional structure of HBP has been published (Iversen et al Nat Struct Biol. 1997 April; 4(4):265-8). It is contained in the azurophilic granulae and secretory vesicles of human neutrophils (Lindmark et al, J Leukoc Biol 1999; 66(4):634-43 and Tapper et al, Blood 2000; 96:2329-2337). It is a multifunctional protein that has been shown to induce vascular leakage by altering the $Ca^{2+}$ balance of the blood vessel cytoskeleton (Gautam et al, Nature Medicine 2001; 7(10):1123-7). The M-protein of group A streptococci (GAS) in complex with fibrinogen has been shown to induce HBP release by stimulation of the B2-integrin receptor of neutrophils (Herwald et al, Cell 2004; 116(3):367-79). LPS can also induce HBP release by an unknown mechanism (Rasmussen et al, FEBS Lett 1996; 390(1):109 12). The sequence of HBP is publically available (for example as NCBI accession no. NP_001691 REGION: 27.248) and is reproduced below as SEQ ID NO. 1

```
                                            SEQ ID NO: 1
IVGGRKARPRQFPFLASIQNQGRHFCGGALIHARFVMTAASCFQSQNPGV

STVVLGAYDLRRRERQSRQTFSISSMSENGYDPQQNLNDLMLLQLDREAN

LTSSVTILPLPLQNATVEAGTRCQVAGWGSQRSGGRLSRFPRFVNVTVTP

EDQCRPNNVCTGVLTRRGGICNGDGGTPLVCEGLAHGVASFSLGPCGRGP

DFFTRVALFRDWIDGVLNNPGP
```

HBP levels in patients suspected of having meningitis have not previously been investigated. The inventors have shown for the first time that levels of HBP are increased in individuals with acute bacterial meningitis. According to the invention there is thus provided a method of identifying whether or not an individual has bacterial meningitis, which method comprises measuring HBP in the individual and thereby determining whether or not the individual has bacterial meningitis.

The invention further provides:
  an agent for the detection of HBP for use in determining whether or not an individual has bacterial meningitis;
  a test kit for use in a method for determining whether or not an individual has bacterial meningitis, which test kit comprises an agent for the detection of HBP in an individual;
  a method of treating an individual for bacterial meningitis comprising:
    (i) determining whether or not an individual has bacterial meningitis using a method of the invention; and
    (ii) administering to an individual identified in (i) as at risk, a therapeutically effective amount of at least one agent suitable for the treatment of bacterial meningitis.

DETAILED DESCRIPTION OF THE INVENTION

Diagnosis

Figure 1:
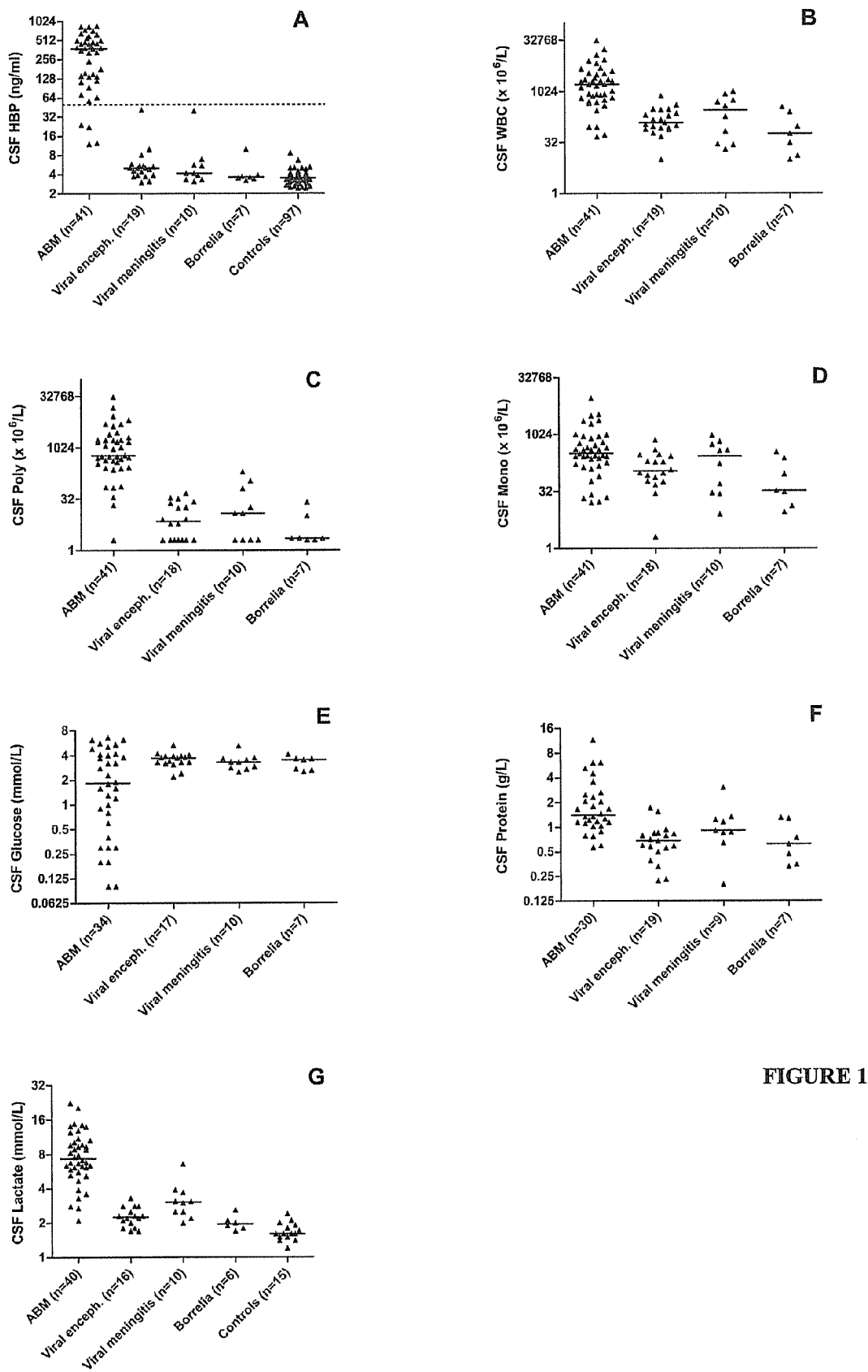
FIG. 1 shows cerebrospinal fluid (CSF) levels of HBP (A), WBC count (B), neutrophil (poly) count (C), mononuclear (mono) count (D), glucose (E), protein (F), and lactate (G) in patients with acute bacterial meningitis (ABM), viral encephalitis, viral meningitis, neuroborreliosis (Borrelia), and patients with normal WBC and no CNS infection (controls). The dotted line indicates a cut-off level of 50 ng/mL for HBP. Median values are given. All scatter plots presented in Log 2 scale.

The present invention relates to a method of identifying whether or not a subject has bacterial meningitis, particularly acute bacterial meningitis. The invention therefore relates to the diagnosis of bacterial meningitis. The invention relates to distinguishing bacterial meningitis from other disorders that cause similar symptoms, particularly viral meningitis or encephalitis (viral meningoencephalitis), and neuroborreliosis.

Traditionally, CSF WBC count has been considered a useful tool for the differential diagnosis of bacterial meningitis, with a low pleocytosis or a relative lymphocytosis considered a sign of nonbacterial cause. However, previous studies have reported that a CSF pleocytosis of >1000 cells only had a sensitivity of 61% and a specificity of 68% as a diagnostic marker of CSF infection in neurosurgical patients. Moreover, although 94% of patients with bacterial meningitis had polymorphonuclear predominance, this criterion only had a specificity of 28%.

Furthermore, in patients with a clinical suspicion of bacterial meningitis, it is not uncommon that antibiotics are instituted prior to lumbar puncture, reducing the chance of a rapid definitive diagnosis through methods such as Gram smear or CSF-culture, and possibly incorrectly prolonging antibiotic therapy in some cases. More significantly, a CSF culture positive for bacterial infection is generally regarded as the gold standard of the diagnosis of bacterial meningitis, and so the risk of misclassification in cases of a negative culture is possible. In short, clinical features of patients with bacterial and viral meningitis may be remarkably similar and cerebrospinal fluid (CSF) findings are typically inconclusive.

The present inventors have for the first time investigated the level of HBP in patients suspected of having meningitis. The inventors have demonstrated that HBP levels are elevated in patients with bacterial meningitis relative to those with viral meningitis or encephalitis, neuroborreliosis or control patients who do not have meningitis. HBP levels are elevated in patients with meningitis caused by a wide range of different bacterial infections. This includes patients with infections acquired following neurosurgical procedures. Since the differential diagnosis of postoperative meningitis/ventriculitis is difficult, HBP will be particularly useful as a diagnostic marker in a neurosurgical setting.

The individual under test is typically suspected of having meningitis. The individual is typically a mammal. The mammal is typically a human or a domestic mammal such as a horse, a cow, a sheep, a dog or a cat. The individual is preferably a human. The individual may typically be suspected of having meningitis because they present with one or more of the following symptoms:

Fever/vomiting; Severe headache; Nuchal rigidity (less common in young children); Photophobia; Phonophobia; Sleepiness (patient typically very sleepy/vacant/difficult to wake); Confusion/delirium; Rash anywhere on the body (not present in all cases); Seizures.

Where the individual subject is a young child or baby, the above symptoms are often absent. Instead, a young child or baby may typically be suspected of having meningitis because they present with one or more of the following symptoms:

Refusal to eat/feed; Irritablility (not wanting to be held/touched); A stiff body, with jerky movements, or floppiness and an inability to stand up; A bulging fontanelle (in subjects up to 6 months old); A high pitched cry or moaning; Leg pain; Cold extremities; Abnormal skin color.

In adults, a severe headache is the most common symptom of meningitis-occurring in almost 90% of cases of bacterial meningitis. The next most common symptom is nuchal rigidity (stiffness of the neck) which occurs in 70% of adult cases. The classic triad of diagnostic signs consists of nuchal rigidity, sudden high fever, and altered mental status; however, all three features are present in only 44-46% of all cases of bacterial meningitis. If none of the three signs is present, meningitis is considered to be unlikely but is not ruled out. Other signs commonly associated with meningitis include photophobia (intolerance to bright light) and phonophobia (intolerance to loud noises).

Other signs which may give rise to a suspicion of meningitis are the presence of positive Kernig's sign or Brudzinski's sign. Kernig's sign is assessed with the patient lying supine, with the hip and knee flexed to 90 degrees. In a patient with a positive Kernig's sign, pain limits passive extension of the knee. A positive Brudzinski's sign occurs when flexion of the neck causes involuntary flexion of the knee and hip. Although Kernig's and Brudzinski's signs are both commonly used to screen for meningitis, the sensitivity of these tests is limited. Another test, known as the "jolt accentuation maneuver" helps determine whether meningitis is present in patients reporting fever and headache. The patient is told to rapidly rotate his or her head horizontally; if this does not make the headache worse, meningitis is unlikely.

The rash symptom mentioned above typically takes the form of a rapidly spreading petechial rash which may precede other symptoms. The rash consists of numerous small, irregular purple or red spots ("petechiae") on the trunk, lower extremities, mucous membranes, conjuctiva, and (occasionally) the palms of the hands or soles of the feet. The rash is typically non-blanching: the redness does not disappear when pressed with a finger or a glass tumbler. Such a rash is generally only present in subjects with meningitis caused by the bacterium *Neisseria meningitidis* (known as "meningococcal meningitis"), although it does occasionally occur in meningitis due to other bacteria.

Other symptoms which may give rise to a suspicion of meningitis may be the skin signs of hand, foot and mouth disease and/or genital herpes, both of which are associated with various forms of viral meningitis.

The individual subject may be suspected of having meningitis because of the presence of one or more risk factors. Risk factors for meningitis include:

Living in a communal environment, particularly an environment in which a large number of individuals are living together for the first time. For example an army barracks during mobilization; a university campus;

Trauma to the skull; particularly a skull fracture that affects the base of the brain or extends towards the sinuses and petrous pyramids An anatomical abnormality, particularly an abnormality allowing continuity between the external environment and the nervous system. Typical examples include cranial or cervical abnormalities such as: Heterotopic brain tissue, Meningioma, Skull base defects (e.g. to the Ethmoid bone, Petrosal bone or Sphenoid sinus), Dermoid cyst/epidermoid cyst/dermal sinus tract, Cranial lymphangiomatosis, Neurenteric cyst, Inner ear abnormality, or Mondini dysplasia, or lumbosacral abnormalities such as Meningocele or Dermal sinus/dermoid cyst;

Presence of a cochlear implant; or another cranial or neurosurgical implant such as cerebral shunt or related device (e.g. an extraventricular drain or Ommaya reservoir);

An impaired immune system/immunodeficiency, for example complement deficiency;

A diagnosis of HIV/AIDS;

A recent neurosurgical operation, for example ventriculoperitoneal shunt or spinal surgery, or other form of cranial or maxillofacial surgery resulting in a CSF leak, or a recent otorhinolaryngological intervention;

Recent or ongoing diagnosis of an infection in the head and/or neck area (a parameningeal infection), such as sinusitis, otitis media, mastoiditis, osteomyelitis, Maffuci's syndrome or Neurofibromatosis type 1;

Recent or ongoing diagnosis of a virus associated with meningitis, such as enterovirus, herpes simplex virus type 1 or 2, varicellae zoster virus (chickenpox/shingles), mumps virus, HIV, Cytomegalovirus, or LCMV.

The present invention involves measuring the level of HBP in an individual. The level of HBP is typically measured in vitro in a sample obtained from an individual. The sample typically comprises a body fluid of an individual. A fluid sample may be a sample of blood, plasma, serum, urine, cerebrospinal fluid or joint fluid. The sample is preferably a cerebrospinal fluid sample.

According to the present invention, an increased level or concentration of HBP compared with the baseline level or concentration indicates that the individual has bacterial meningitis. The baseline level is typically the level of HBP in an individual who is suspected of having meningitis, but is subsequently confirmed to not have bacterial meningitis.

For example the inventors have shown that, when the level of HBP is measured by determining the concentration of HBP in a CSF sample obtained from an individual suspected of having meningitis, individuals who are subsequently shown to have viral meningoencephalitis (viral meningitis or encephalitis) have a median HBP concentration of about 4.7 ng/ml, individuals who are subsequently shown to have neuroborreliosis have a median HBP concentration of about 3.6 ng/ml, and individuals who present with symptoms leading to a suspicion of meningitis, but are subsequently shown not to have meningitis, have a median HBP concentration of about 3.5 ng/ml. The median HBP concentration for all categories of individual who are suspected of having meningitis but do not have bacterial meningitis is about 3.6 ng/ml.

In more detail, the average HBP concentrations in ng/ml for each category of individual are as follows: (i) individuals with viral meningitis/encephalitis (n=29): mean 7.3, median 4.7, range 3.0-41.0; (ii) individuals with viral meningitis or borrelia (n=36): mean 6.7, median 4.4, range 3-41; and (iii) all nonbacterial meningitis individuals (n=133): mean 4.5, median 3.6, range 2.4-41.

The baseline level or concentration of HBP may therefore typically be in the range of 3 to 5 ng/ml. For example, the baseline level or concentration of HBP may be about 3 ng/ml, 4 ng/ml or 5 ng/ml.

According to the present invention, the increase in HBP level or concentration which is associated with a diagnosis of bacterial meningitis is an increase of at least 3 fold, 4 fold, 5 fold or 10 fold relative to the baseline level or concentration. The increase in HBP level or concentration is preferably at least 4 fold relative to the baseline level or concentration.

In the present invention, an increased level or concentration of HBP associated with a diagnosis of bacterial meningitis is typically greater than about 11 ng/ml, or greater than about 12 ng/ml, 13 ng/ml, 14 ng/ml, 15 ng/ml, 20 ng/ml, 23 ng/ml, 25 ng/ml, 30 ng/ml, 32 ng/ml, 35 ng/ml, 40 ng/ml, 41 ng/ml, 42 ng/ml, 43 ng/ml, 44 ng/ml, 45 ng/ml, 46 ng/ml, 47 ng/ml, 48 ng/ml, 49 ng/ml, 50 ng/ml, 51 ng/ml, 52 ng/ml, 53 ng/ml, 54 ng/ml, 55 ng/ml, 56 ng/ml, 57 ng/ml, 58 ng/ml, 59 ng/ml 60 ng/ml, 70 ng/ml, 80 ng/ml, 90 ng/ml, 100 ng/ml, 200 ng/ml, 300 ng/ml, 400 ng/ml, 500 ng/ml, 600 ng/ml, 700 ng/ml, 800 ng/ml, or 900 ng/ml. The increased concentration of HBP associated with a diagnosis of bacterial meningitis is preferably greater than about 50 ng/ml.

Detection of HBP

The invention is typically carried out by measuring the level of HBP in vitro in a sample obtained from the individual. The sample typically comprises a body fluid of the individual. A fluid sample may be a sample of blood, plasma, serum, urine, cerebrospinal fluid or joint fluid. The sample is preferably a cerebrospinal fluid sample.

The sample is typically processed prior to being assayed, for example by centrifugation. The sample may also be typically stored prior to assay, preferably below −70° C.

Standard methods known in the art may be used to assay the level of HBP. These methods typically involve using an agent for the detection of HBP. The agent typically binds specifically to HBP. The agent may be an antibody specific for HBP, an aptamer that binds to HBP, a serine proteinase inhibitor such as aprotinin, for example as described in Petersen et al, Eur J Biochem 1993; 271-9, or a soluble fragment of an integrin, for example as described in Cai and Wright, S. D. J Exp Med 1996; 184:213-23. By specific, it will be understood that the agent or antibody binds to HBP with no significant cross-reactivity to any other molecule, particularly any other protein. For example, an agent or antibody specific for HBP will show no significant cross-reactivity with human neutrophil elastase. Cross-reactivity may be assessed by any suitable method.

An antibody used in the method of the invention may either be a whole antibody or a fragment thereof which is capable of binding to HBP. The antibody may be monoclonal. Such a whole antibody is typically an antibody which is produced by any suitable method known in the art. For example, polyclonal antibodies may be obtained by immunising a mammal, typically a rabbit or a mouse, with HBP under suitable conditions and isolating antibody molecules from, for example, the serum of said mammal. Monoclonal antibodies may be obtained by hybridoma or recombinant methods.

Hybridoma methods involve immunising a mammal, typically a rabbit or a mouse, with HBP under suitable conditions, then harvesting the spleen cells of said mammal and fusing them with myeloma cells. The mixture of fused cells is then diluted and clones are grown from single parent cells. The antibodies secreted by the different clones are then tested for their ability to bind to HBP, and the most productive and stable clone is then grown in culture medium to a high volume. The secreted antibody is collected and purified.

Recombinant methods involve the cloning into phage or yeast of different immunoglobulin gene segments to create libraries of antibodies with slightly different amino acid sequences. Those sequences which give rise to antibodies which bind to HBP may be selected and the sequences cloned into, for example, a bacterial cell line, for production.

Typically the antibody is a mammalian antibody, such as a primate, human, rodent (e.g. mouse or rat), rabbit, ovine, porcine, equine or camel antibody. The antibody may be a camelid antibody or shark antibody. The antibody may be a nanobody. The antibody can be any class or isotype of antibody, for example IgM, but is preferably IgG.

The fragment of whole antibody that can be used in the method comprises an antigen binding site, e.g. Fab or F(ab)2 fragments or ScFV. The whole antibody or fragment may be associated with other moieties, such as linkers which may be used to join together 2 or more fragments or antibodies. Such linkers may be chemical linkers or can be present in the form of a fusion protein with the fragment or whole antibody. The linkers may thus be used to join together whole antibodies or fragments which have the same or different binding specificities, e.g. that can bind the same or different polymorphisms. The antibody may be a bispecific antibody which is able to bind to two different antigens, typically any two of the polymorphisms mentioned herein. The antibody may be a 'diabody' formed by joining two variable domains back to back. In the case where the antibodies used in the method are present in any of the above forms which have different antigen binding sites of different specificities then these different specificities are typically to polymorphisms at different positions or on different proteins. In one embodiment the antibody is a chimeric antibody comprising sequence from different natural antibodies, for example a humanised antibody.

Methods to assess HBP level typically involve contacting a sample with an agent or antibody capable of binding specifically to HBP. Such methods may include dipstick assays and Enzyme-linked Immunosorbant Assay (ELISA). Typically dipsticks comprise one or more antibodies or proteins that specifically bind HBP. If more than one antibody is present, the antibodies preferably have different non-overlapping determinants such that they may bind to HBP simultaneously.

ELISA is a heterogeneous, solid phase assay that requires the separation of reagents. ELISA is typically carried out using the sandwich technique or the competitive technique. The sandwich technique requires two antibodies. The first specifically binds HBP and is bound to a solid support. The second antibody is bound to a marker, typically an enzyme conjugate. A substrate for the enzyme is used to quantify the HBP-antibody complex and hence the amount of HBP in a sample. The antigen competitive inhibition assay also typically requires an HBP-specific antibody bound to a support. An HBP-enzyme conjugate is added to the sample (containing HBP) to be assayed. Competitive inhibition between the HBP-enzyme conjugate and unlabeled HBP allows quantification of the amount of HBP in a sample. The solid supports for ELISA reactions preferably contain wells.

The present invention may also employ methods of measuring HBP that do not comprise antibodies. High Performance Liquid Chromatography (HPLC) separation and fluorescence detection is preferably used as a method of determining the HBP level. HPLC apparatus and methods as described previously may be used (Tsikas D et al. J Chromatogr B Biomed Sci Appl 1998; 705:174-6) Separation during HPLC is typically carried out on the basis of size or charge. Prior to HPLC, endogenous amino acids and an internal standard L-homoarginine are typically added to assay samples and these are phase extracted on CBA cartridges (Varian, Harbor City, Calif.). Amino acids within the samples are preferably derivatized with o-phthalaldehyde (OPA). The accuracy and precision of the assay is preferably determined within quality control samples for all amino acids.

The invention further provides a diagnostic kit that comprises means for measuring the HBP level in an individual and thereby determining whether or not the individual has bacterial meningitis. The kit typically contains one or more antibodies that specifically bind HBP. For example, the kit may comprise a monoclonal antibody, a polyclonal antibody, a single chain antibody, a chimeric antibody, a CDR-grafted antibody or a humanized antibody. The antibody may be an intact immunoglobulin molecule or a fragment thereof such as a Fab, F(ab')$_2$ or Fv fragment. If more than one antibody is present, the antibodies preferably have different non-overlapping determinants such that they may bind to HBP simultaneously.

The kit may additionally comprise means for the measurement of other laboratory or clinical parameters. For example the kit may comprise means for measuring the WBC count in an individual, and/or the level or concentration of one or more of lactate, glucose and C-reactive protein.

The kit may additionally comprise one or more other reagents or instruments which enable any of the embodiments of the method mentioned above to be carried out. Such reagents or instruments include one or more of the following: suitable buffer(s) (aqueous solutions), means to isolate HBP from sample, means to obtain a sample from the individual (such as a vessel or an instrument comprising a needle) or a support comprising wells on which quantitative reactions can be done. The kit may, optionally, comprise instructions to enable the kit to be used in the method of the invention or details regarding which individuals the method may be carried out upon.

Therapy

The present invention also relates to the treatment of an individual identified by a method of the invention as having bacterial meningitis. Thus, a substance for use in the treatment of bacterial meningitis may be used in the manufacture of a medicament for use in the treatment of an individual identified by a method of the invention as having bacterial meningitis. The condition of an individual identified by a method of the invention as having bacterial meningitis can therefore be improved by administration of such a substance. A therapeutically effective amount of a substance useful for the treatment of bacterial meningitis may be given to an individual identified by a method of the invention as in need thereof. Substances suitable for the treatment of bacterial meningitis typically include one or more antibiotics and/or one or more intravenous fluids and/or one anti-inflammatory agents. The one or more antibiotics are typically broad spectrum antibiotics. The broad spectrum antibiotics are typically selected from one or more aminoglycosides, glycopeptides, cephalosporins, fluoroquinolones, lincosamides, macrolides, penicillins, carbapenems, sulfonamides, or tetracyclins. For example, suitable antibiotics include, but are not limited to, Gentamicin, Kanamycin, Neomycin, Streptomycin, Tobramycin, Vancomycin, Cefazolin, Cephalexin, Cephapirin, Cephradine, Cefuroxime, Cefixime, Cefotaxime, Ceftazidime, Ceftizoxime, Ceftriaxone, Ciprofloxacin, Levofloxacin, Ofloxacin, Clindamycin, Azithromycin, Clarithromycin, Erythromycin, Amoxicillin, Ampicillin, Ampicillin-Sulbactam, Cloxacillin, Dicloxacillin, Mezlocillin, Nafcillin, Oxacillin, Penicillin G Benzathine, Penicillin G Potassium, Penicillin G Procaine, Penicillin V Potassium, Piperacillin, Ticarcillin, Ticarcillin-Clavulanate potassium, Imipenem, Meropenem, Pyrimethamine-Sulfadoxine, Sulfadizine, Sulfisoxazole, Sulfinethoxazole, Trimethoprim-sulfamethoxazole, Chlortetracycline, Doxycycline, and Tetracycline.

The one or more anti-inflammatory agents are typically corticosteroids, most typically Dexamethasone, Betamethasone, Hydrocortisone, or Methylprednisolone.

A substance useful the treatment of bacterial meningitis according to the invention is typically formulated for administration in the present invention with a pharmaceutically acceptable carrier or diluent. The pharmaceutical carrier or diluent may be, for example, an isotonic solution. For example, solid oral forms may contain, together with the active substance, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film-coating processes.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active substance, a pharmaceutically acceptable carrier, e.g. sterile water, olive oil, ethyl oleate, glycols, e.g. propylene glycol, and if desired, a suitable amount of lidocaine hydrochloride.

Solutions for intravenous administration or infusion may contain as carrier, for example, sterile water or preferably they may be in the form of sterile, aqueous, isotonic saline solutions.

A therapeutically effective amount of a substance used for the treatment of bacterial meningitis is administered to a patient identified according to a method of the invention. The dose, for example of an antibiotic, may be determined according to various parameters, especially according to the substance used; the age, weight and condition of the patient to be treated; the route of administration; and the required regimen. Again, a physician will be able to determine the required route of administration and dosage for any particular patient. A typical daily dose is from about 0.1 to 50 mg per kg of body weight, according to the activity of the specific antibiotic, the age, weight and conditions of the subject to be treated and the frequency and route of administration. Preferably, daily dosage levels are from 5 mg to 2 g. That dose may be provided as a single dose or may be provided as multiple doses, for example taken at regular intervals, for example 2, 3 or 4 doses administered daily.

The following Example illustrates the invention:

Example

Methods

Study Population

CSF samples from a total of 174 patients from two different cohorts were analyzed. One hundred fifty-nine adult patients with clinically suspected meningitis, who underwent a lumbar puncture, were enrolled in a prospective study at the Clinic for Infectious Diseases, Lund University Hospital, Sweden, between March 2006 and November 2009. Fourteen patients with CSF pleocytosis due to suspected viral CNS infection or neuroborreliosis but without a proven microbiological diagnosis were excluded, and therefore a total of 145 patients were included. In addition, another retrospective cohort of 16 patients with bacterial meningitis and 13 patients with HSV-1 encephalitis collected between 1995 and 2004 at the Clinic for Infectious Diseases, Sahlgrenska University Hospital, Gothenburg, Sweden, was included. This was done to enlarge the study material, especially the number of patients with HSV-1 encephalitis who were scarce in the prospectively collected patient material, and also to increase the number of more unusual bacterial meningitis pathogens. The work-ups and final diagnoses of the patients were made by attending physicians unaware of the HBP results, using standard laboratory and microbiological tests. The patients were categorized into five groups: 1. Acute bacterial meningitis, 2. Viral encephalitis, 3. Viral meningitis, 4. Neuroborreliosis, 5. Control patients with normal CSF WBC count.

Classification of bacterial meningitis was based on the criteria of Durand et al. (N Engl J Med 1993 Jan. 7; 328(1):21-8), where compatible clinical features, a cerebrospinal fluid pleocytosis and one of the following: a) positive CSF culture; b) negative CSF culture, but either a positive CSF antigen test, identification of bacteria on Gram stain of CSF, a positive 16S rDNA PCR, or a positive blood culture, was required for the diagnosis of bacterial meningitis. Only patients who had received adequate antibiotic treatment for less than 48 hours were included.

The diagnosis of viral CNS diseases were based on acute onset of symptoms compatible with viral meningitis or encephalitis, exclusion of bacterial CNS infection, and either: a) a positive PCR result for virus DNA or RNA in the CSF or, b) specific serum IgM antibodies for Tick-borne encephalitis (TBE) virus. A CSF pleocytosis combined with detection of specific *B. burgdorferi* antibodies in the CSF were required for the diagnosis of neuroborreliosis. The ethics committees of Lund and Gothenburg Universities approved of the study and all samples were taken with the informed consent of the participants.

Analysis of Cerebrospinal Fluid Concentrations of HBP and Other CSF Markers

CSF samples were collected by the attending physician as part of routine patient management. The concentration of HBP was determined by ELISA using routine methods. Briefly, microtiter plates (NUNC) were coated with a mouse monoclonal antibody directed against human HBP (2F23A) at 1.1 µg/mL in coating buffer (0.05 M $NaHCO_3$, pH 9.6). Plates were washed with PBST (phosphate-buffered saline containing 0.05% Tween) and blocked with 2% bovine serum albumin (Sigma) in PBST. Patient CSF samples diluted 1/40 in sample buffer (1 M NaCl) was then added to the wells in duplicate and incubated for 60 min at 37° C. Each plate also contained calibration samples of known concentration of recombinant human HBP (0-600 ng/mL). After washing, plates were incubated with a polyclonal rabbit antiserum towards human HBP diluted 1/7000. Bound antibodies were detected by incubation with peroxidase-conjugated antibody against rabbit IgG (Bio-Rad) (1/3000). Plates were developed and the optical density at 405 nm was determined using routine methods. The level of HBP in each patient sample was determined by calculating the mean optical densities of the duplicates which were correlated to the results from the standard curve. The day-to-day variation of the assay had a coefficient of variance of <10%. Analyses of WBC, glucose, and protein in CSF are standard procedures and were performed as routine tests at the laboratories of Clinical Chemistry at Lund and Sahlgrenska University Hospitals. The concentrations of lactate in CSF samples were analyzed on a Cobas c501 (Amazonas) with reagents according to the manufacturer's instructions.

Statistical Analysis

Comparisons between two different groups were made by the non-parametric Mann-Whitney U test, and in the comparisons between more than two groups the non-parametric Kruskal-Wallis one-way ANOVA analysis was used. A two-tailed p-value of <0.05 was considered statistically significant. Spearmans non-parametric correlation coefficient was used for calculating correlations between patient groups. Receiver-operating characteristic (ROC) curves and the area under the curve (AUC) were constructed to illustrate various cut-off levels for HBP. AUC values are reported with the 95% confidence interval (95% CI). The SPSS 14.0 software system (SPSS) and Graph-Pad Prism 5.0 (Graph-Pad software, La Jolla, Calif.) were used for calculations.

Results

Patient Characteristics

Forty-one patients were classified as having bacterial meningitis, 19 viral encephalitis, 10 viral meningitis, 7 neuroborreliosis, and 97 patients had a normal CSF WBC count ($<5 \times 10^6$/L) and were regarded as a control group without CNS infection. Demographic characteristics (age and sex) were similar between the four patient groups with infections (Table 1). In the control group the male/female ratio was 41/56 with a mean age of 42 years (range 18-85 years). Thirty-nine out of the 97 patients in the control group had fever and headache without CNS infection, and were later diagnosed with various bacterial and viral infections. In the bacterial meningitis group (n=41), there were 37 patients with acute community-acquired bacterial meningitis, and four patients with postoperative bacterial meningitis after neurosurgery. Twenty-three patients (56%) had a positive CSF culture, 13 a positive 16S rDNA, one a positive CSF antigen test, and four patients had positive blood cultures. Bacterial etiologies were *S. pneumoniae* (n=16), *N. meningitidis* (n=5), *Listeria monocytogenes* (n=5), *Haemophilus influenzae* (n=2), *Escherichia coli* (n=2), group A streptococci (n=2), group G streptococci (n=2), and *Staphylococcus aureus, Staphylococcus epidermidis,* α-streptococci, *Enterococcus faecalis, Gemella* species, *Klebsiella pneumoniae,* and *Pseudomonas aeruginosa*, one each. In the prospective part of the bacterial meningitis group, the 28 days mortality was 16%. In the group of viral CNS infections, there were 19 patients with encephalitis (HSV-1 n=15, TBE n=4), and ten patients with meningitis (Enterovirus n=4, Varicella-zoster virus (VZV) n=3, Herpes simplex virus type 2 (HSV-2) n=2, and Cytomegalovirus (CMV) n=1). Among the patients with HSV-1 encephalitis five patients had not received treatment with aciclovir at the time of lumbar puncture, and the median time of aciclovir treatment before lumbar puncture was 48 hours (range 0-8 days).

CSF Characteristics

The total WBC, poly, and mono counts in CSF, were significantly higher in the bacterial meningitis group compared to the viral CNS infection and neuroborreliosis groups (p<0.01), although there were considerable overlapping between the groups (FIG. 1B-D). Also, eleven patients with bacterial infection (27%) had a mononuclear predominance, and 17 patients (41%) had a total CSF WBC count below 1000 cells (FIG. 1B), while two patients had neutrophil cell predominance in the viral CNS infection groups. CSF glucose levels were significantly lower (p=0.01), whereas CSF protein and lactate levels were significantly higher (p<0.01) in the bacterial meningitis group as compared to the three other groups (FIG. 1E-G). There were no significant differences between the groups of viral meningitis or encephalitis and neuroborreliosis when comparing CSF characteristics (p>0.05) (FIG. 1B-F).

CSF Levels of HBP

The levels of HBP were significantly higher (p<0.01) in patients with bacterial meningitis (median 376 ng/mL, range 12-858 ng/mL) compared to patients with viral encephalitis (median 5.0 ng/mL, range 3.0-41 ng/mL), viral meningitis (median 4.2 ng/mL, range 3.1-40 ng/mL), neuroborreliosis (median 3.6 ng/mL, range 3.2-10 ng/mL), and patients in the control group without pleocytosis in CSF (median 3.5 ng/mL, range 2.4-8.7 ng/mL) (FIG. 1A).

Figure 2:
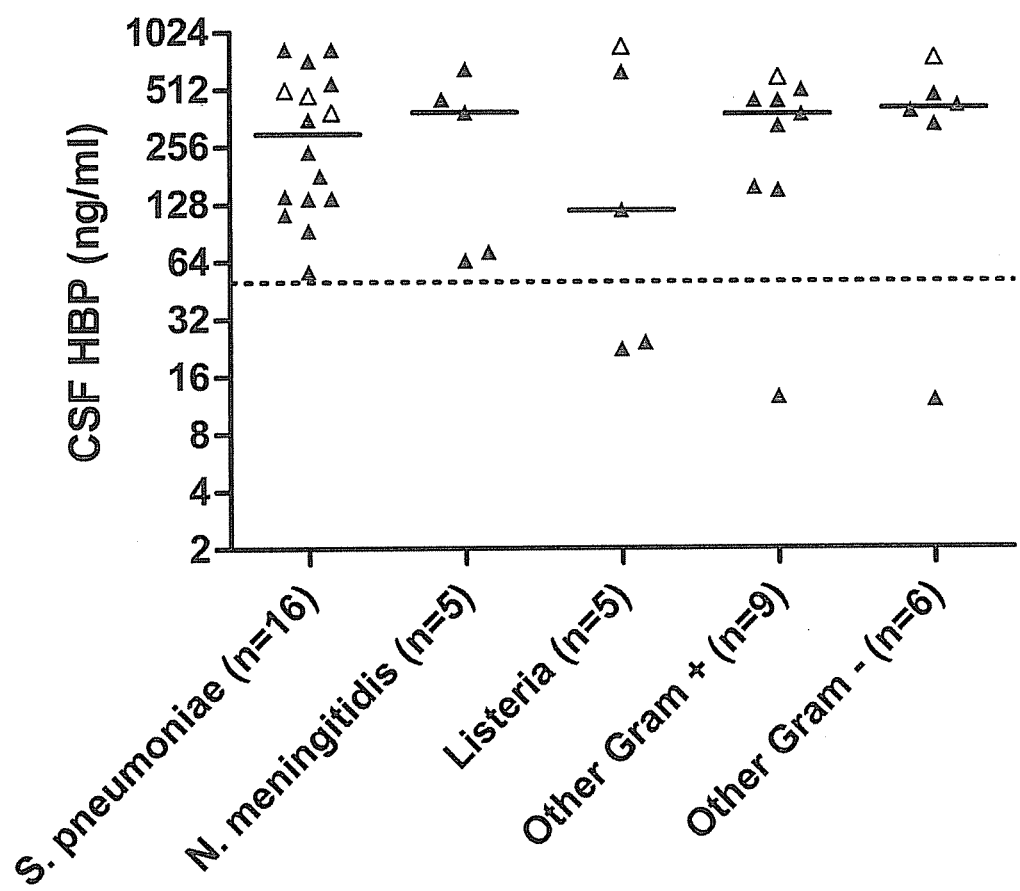
FIG. 2 shows Levels of HBP and bacterial etiology. There was no significant difference in HBP levels when comparing different bacterial species. Open triangles indicate patients who died within 28 days and the dotted line a cut-off level of 50 ng/mL. Median values are given. Scatter plot presented in Log 2 scale.

Thirty-seven (90%) of the 41 patients with bacterial meningitis had a HBP concentration above 50 ng/mL, which exceeded the highest HBP levels found in the three other groups (FIG. 1A). Among the four patients with CSF HBP levels below 50 ng/ml there were CSF cultures positive for *L. monocytogenes* in two cases, a positive CSF antigen test for *H. influenzae* in one patient, and in one patient blood cultures were positive for group A streptococci (FIG. 2). In 15 of the 41 patients, the CSF samples were collected before the institution of antibiotics. Eleven, 8, and 7 patients had received adequate antibiotic treatment 1-12, 12-24, and 24-48 hours prior to CSF sample collection, respectively. Of the 26 patients who received antibiotic treatment up to 24 h before sampling, 24 had a HBP level exceeding 50 ng/mL. Fourteen different bacterial agents were found, all in combination with an elevated HBP level. All six non-survivors had elevated HBP levels (>385 ng/mL) (FIG. 2).

The highest HBP levels found in the group of viral infections were in one patient with HSV-1 encephalitis (41 ng/mL) and in another patient with HSV-2 meningitis (40 ng/mL) (FIG. 1A). There was no correlation between the duration of aciclovir treatment in the HSV-1/2 infected patients and the levels of HBP, lactate, WBC, poly or mono.

Figure 3:
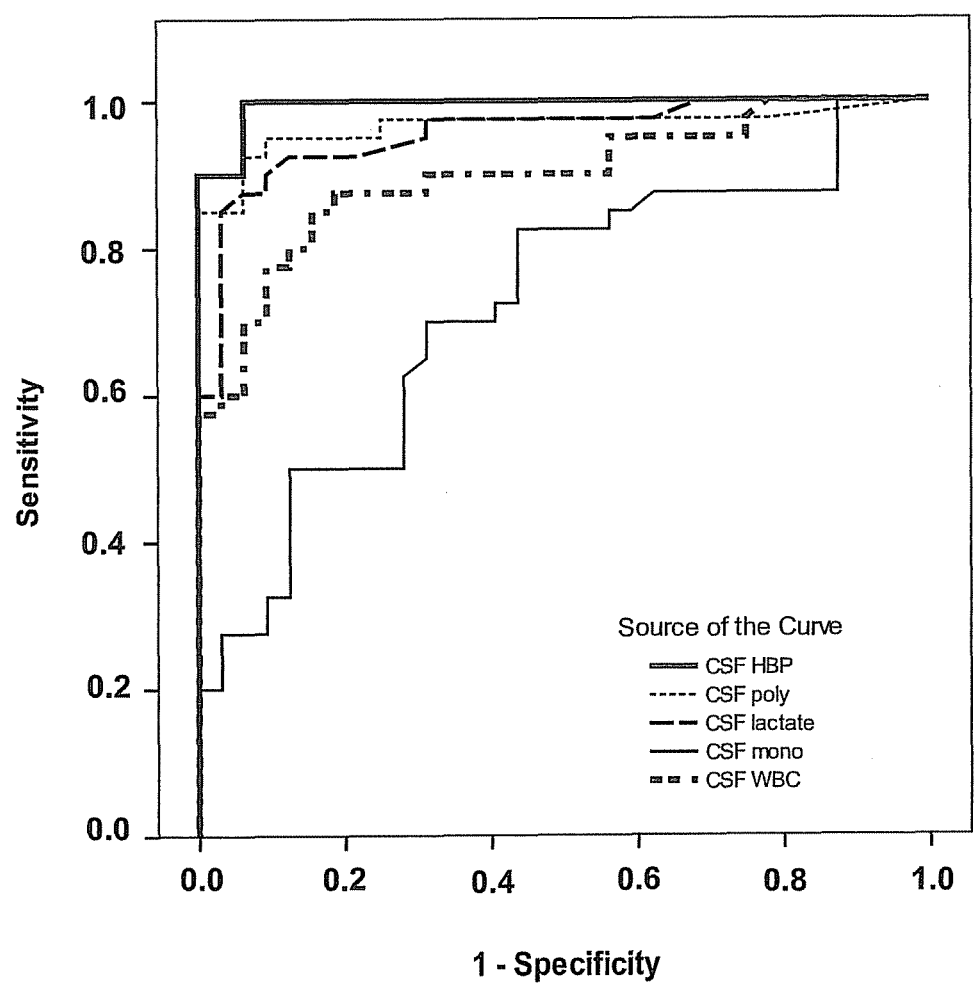
FIG. 3 shows Receiver-operating characteristics (ROC) curves for differentiating bacterial meningitis from other CNS infections using HBP (thick solid line), lactate (thin, dashed line), neutrophils (poly: thin, dotted line), mononuclear cells (mono: thin solid line), and total WBC (thick, irregular dotted line) in cerebrospinal fluid (CSF). Differentiation is between bacterial meningitis (n=40) and viral CNS infection or neuroborreliosis (n=35). Areas under the ROC curves were 0.994 (95% confidence interval (CI), 0.984-1.004) for HBP, 0.955 (95% CI, 0.911-1.000) for lactate, 0.966 (95% CI, 0.920-1.011) for poly, 0.729 (95% CI, 0.614-0.843) for mono, and 0.898 (95% CI, 0.826-0.970) for total WBC.

A cut-off level of 50 ng/mL had a sensitivity of 90% and a specificity of 100% for the detection of bacterial meningitis. A receiver-operating characteristics (ROC) curve showed an area under the curve (AUC) value of 0.994 for HBP, making it the best marker in differentiating between bacterial and non-bacterial meningitis or neuroborreliosis in this study, followed by lactate and neutrophils (poly) (FIG. 3). There was a significant correlation (p<0.01) between HBP and lactate, WBC, poly, mono, protein, and ICU days.

Discussion

Clinical features of patients with bacterial and viral infections of the CNS may be remarkably similar and CSF findings inconclusive. This is the first study investigating the presence of neutrophil-derived HBP in the CSF and our findings show that HBP is a useful diagnostic marker in the discrimination between patients with bacterial and viral CNS infections. Traditionally, pleocytosis in the CSF has been considered a useful tool in differentiating between bacterial and viral etiology, with a low pleocytosis or a relative lymphocytosis indicating nonbacterial origin. However, it is important to recognize that there have been several reports of documented cases of bacterial meningitis with absence of pronounced CSF pleocytosis. Ross et al (*J Neurosurg* 1988 November; 69(5):669-74) reported that a CSF pleocytosis of >1000×10$^6$/L cells only had a sensitivity of 61% and a specificity of 68% as a diagnostic marker of CSF infection in post-operative neurosurgical patients. Moreover, although 94% of patients with bacterial meningitis had neutrophil predominance, this criterion only had a specificity of 28%. In our study, 61% of the patients with bacterial meningitis and 3% of those with viral CNS infection had a CSF pleocytosis of >1000×10$^6$/L cells. Neutrophil predominance was found in 73% and 7% of the patients with bacterial meningitis and viral CNS infection, respectively.

In patients with a clinical suspicion of bacterial meningitis, it is not uncommon that antibiotics are instituted prior to lumbar puncture, reducing the chance of a microbiological diagnosis, and possibly prolonging antibiotic therapy in some cases. This was seen in the present study, where 64% of the patients received antibiotics up to 48 hours prior to lumbar puncture. However, 24 of these 26 patients still had an HBP level exceeding 50 ng/mL. A positive CSF culture is the gold standard in the diagnosis of bacterial meningitis, and the risk of misclassification in cases of a negative culture is possible. The fact that 21 out of the 23 patients with a positive CSF culture had elevated HBP levels (>50 ng/mL), further supports the use of HBP as a diagnostic marker. An interesting finding was that patients with sub-acute bacterial meningitis caused by *B. burgdorferi* had low HBP levels in the CSF. Neuroborreliosis patients often have a relatively mild disease and are rarely hospitalized. In the bacterial meningitis group, the most prevalent bacterial agents were *S. pneumoniae, N. meningitidis*, and *L. monocytogenes*, which is in accordance with other studies. However, there were 14 different bacterial species found among the patients in this study, and a significant HBP release was induced in all of these cases. Thus, most bacterial species seem capable of this specific neutrophil activation, which has also been shown in patients with severe sepsis. Four patients in the bacterial meningitis group had neurosurgical post-operative CNS infection caused by *P. aeruginosa, E. coli, E. faecalis*, and *S. epidermidis*, and all patients had elevated HBP-levels. The diagnosis of postoperative meningitis/ventriculitis can be a diagnostic challenge, so HBP will be a particularly useful marker in a neurosurgical setting.

Four patients with bacterial meningitis had a HBP level below 50 ng/mL. One was caused by group A streptococci found in blood culture, and another was caused by *H. influenzae* diagnosed by a positive antigen test. These patients both had negative CSF cultures. The CSF total WBC count in these cases were 300 and 700×10$^6$/L, the lactate levels were 2.7 and 2.1 mmol/L, respectively, and the CSF samples were collected between 24 and 48 hours after adequate antibiotic treatment. The other two patients with HBP levels below 50 ng/mL had bacterial meningitis due to *L. monocytogenes*, with positive CSF cultures, and samples collected at the time of antibiotic institution. CSF lactate levels were 2.8 and 3.9 mmol/L and CSF WBC exceeded 1000×10$^6$/L. *L. monocytogenes* is a facultative intracellular bacteria that causes both meningitis and encephalitis in humans and differs in its mechanisms of invasion and subsequent life cycle compared to the other common bacterial meningitis pathogens. A total of five patients were diagnosed with *L. monocytogenes* meningitis. Of these, the two patients with only moderately elevated HBP levels also had a more benign disease with normal consciousness, and not requiring ICU treatment. In the viral CNS infection group, two patients had considerably higher HBP concentrations (41 ng/mL and 40 ng/mL) than the others. One had HSV-2 meningitis with a total WBC of 496×10$^6$/L, and a significantly elevated lactate level of 6.6 mmol/L, in the CSF. The other patient had HSV-1 encephalitis with moderately elevated CSF-WBC (84) and -lactate (2.3). Both had an uncomplicated course with aciclovir treatment.

HBP induces vascular leakage and edema formation, and brain edema is a serious and sometimes fatal complication in bacterial meningitis. Similar to previous studies, there was 16% mortality in the prospective part of this study. However, all non-survivors had strongly elevated HBP levels (>385 ng/mL). Considering the effect of HBP on endothelial cells with subsequent vascular leakage, this indicates a role for HBP in the development of brain edema in bacterial meningitis. Previous studies have shown that treatment with both heparin and monoclonal CD 18 antibodies blocks the β2-integrin receptor on neutrophils responsible for HBP release. These treatments inhibit leukocyte rolling, adhesion and activation, which reduces brain edema and mortality in rat and rabbit models of pneumococcal meningitis. Hypothetically, this effect could be related to the blocking of the vascular leakage induced by HBP.

In conclusion, this study shows that HBP is elevated in CSF in patients with acute bacterial meningitis. Better diagnostic accuracy in differentiating between bacterial and viral CNS infection will allow the clinician to start adequate treatment earlier.

TABLE 1

Characteristics of the study population
"Initial antibiotic treatment" refers to patients receiving initial antibiotics on suspicion of acute bacterial meningitis.

| Characteristics | Bacterial meningitis (n = 41) | Viral encephalitis (n = 19) | Viral meningitis (n = 10) | Neuro-borreliosis (n = 7) |
|---|---|---|---|---|
| Sex (M/F) | 20/21 | 10/9 | 6/4 | 3/4 |
| Age (mean, (range)) | 51 (18-82) | 55 (30-80) | 43 (22-83) | 53 (18-74) |
| Steroid treatment-no. (%) | 25 (61) | 6 (32) | 1 (10) | 0 |
| Initial antibiotic treatment$^a$-no. (%) | 39 (95) | 7 (37) | 3 (30) | 1 (14) |
| Antibiotic treatment prior to sample collection-no. (%) | 26 (64) | 8 (42) | 2 (20) | 0 |

TABLE 1-continued

Characteristics of the study population
"Initial antibiotic treatment" refers to patients receiving initial
antibiotics on suspicion of acute bacterial meningitis.

| Characteristics | Bacterial meningitis (n = 41) | Viral encephalitis (n = 19) | Viral meningitis (n = 10) | Neuro-borreliosis (n = 7) |
|---|---|---|---|---|
| Comorbidity-no. (%) | 21 (51) | 4 (21) | 1 (10) | 2 (29) |
| Length of hospital stay (days) (mean, (range)) | 18.8 (3-40) | 19.3 (10-39) | 5.9 (0-18) | 5 (4-6) |
| Number of pat. in the ICU-no. (%) | 36 (88) | | | |

The invention claimed is:

1. A method of distinguishing acute bacterial meningitis infection from viral meningitis, encephalitis, neuroborreliosis or absence of meningitis infection, the method comprising:
   providing a cerebrospinal fluid sample obtained from an individual suspected of having meningitis;
   contacting the sample with an antibody which binds specifically to Heparin Binding Protein (HBP; Cationic Anti-microbial Protein 37; Azurocidin);
   quantitating the amount of antibody-HBP complex to measure the HBP level in the sample; and
   detecting acute bacterial meningitis infection at 90% Sensitivity or greater and at 93% Specificity or greater based on the measured HBP level in the cerebrospinal fluid to distinguish in the individual an acute bacterial meningitis infection from viral meningitis, encephalitis, neuroborreliosis or absence of meningitis infection.

2. The method according to claim 1, wherein the individual is a mammal.

3. The method according to claim 2, wherein the mammal is a human.

4. The method according to claim 3, wherein the detecting acute bacterial meningitis infection is at 90% Sensitivity or greater and at about 100% Specificity based on the measured HBP level in the cerebrospinal fluid.

5. The method according to claim 3, wherein the detecting of acute bacterial meningitis infection at about 90% Sensitivity or greater and 93% Specificity or greater is determined by a Receiver Operating Characteristic (ROC).

6. The method according to claim 3, wherein the 90% Sensitivity or greater and about 100% Specificity for detecting acute bacterial meningitis infection is a threshold value of about 50 ng/mL HBP in the cerebrospinal fluid.

7. The method according to claim 3, wherein the cerebrospinal fluid sample is obtained by lumbar puncture.

8. The method according to claim 3, wherein the individual has received prophylactic antibiotic treatment but has not been confirmed as having bacterial meningitis infection.

9. The method according to claim 8, wherein the individual has received antibiotic treatment for less than 48 hrs.

10. The method according to claim 3, wherein quantitating the amount of antibody bound to HBP is by enzyme linked immunosorbent assay (ELISA).

11. The method according to claim 3, wherein quantitating the amount of antibody bound to HBP is by a dipstick assay, wherein the dipstick comprises an antibody which binds specifically to HBP.

12. The method according to claim 3, wherein the individual has recently undergone a neurosurgical operation.

13. The method according to claim 3 wherein the individual has a history of skull trauma and/or an anatomical abnormality affecting the cranial, cervical or lumbosacral regions.

14. The method according to claim 3, wherein the individual is immunocompromised; the individual has a cochlear implant; the individual has a cranial or neurosurgical implant, or any combination thereof.

15. The method according to claim 3, further comprising determining levels of one or more of: white blood cell count, neutrophil count, glucose, and protein in the cerebrospinal fluid sample.

\* \* \* \* \*

SEQUENCE LISTING

<160> NUMBER OF SEQ ID NOS: 1

<210> SEQ ID NO 1
<211> LENGTH: 222
<212> TYPE: PRT
<213> ORGANISM: homo sapiens

<400> SEQUENCE: 1

```
Ile Val Gly Gly Arg Lys Ala Arg Pro Arg Gln Phe Pro Phe Leu Ala
1               5                   10                  15

Ser Ile Gln Asn Gln Gly Arg His Phe Cys Gly Gly Ala Leu Ile His
            20                  25                  30

Ala Arg Phe Val Met Thr Ala Ala Ser Cys Phe Gln Ser Gln Asn Pro
        35                  40                  45

Gly Val Ser Thr Val Val Leu Gly Ala Tyr Asp Leu Arg Arg Arg Glu
    50                  55                  60

Arg Gln Ser Arg Gln Thr Phe Ser Ile Ser Ser Met Ser Glu Asn Gly
65                  70                  75                  80

Tyr Asp Pro Gln Gln Asn Leu Asn Asp Leu Met Leu Leu Gln Leu Asp
                85                  90                  95

Arg Glu Ala Asn Leu Thr Ser Ser Val Thr Ile Leu Pro Leu Pro Leu
            100                 105                 110

Gln Asn Ala Thr Val Glu Ala Gly Thr Arg Cys Gln Val Ala Gly Trp
        115                 120                 125

Gly Ser Gln Arg Ser Gly Gly Arg Leu Ser Arg Phe Pro Arg Phe Val
    130                 135                 140

Asn Val Thr Val Thr Pro Glu Asp Gln Cys Arg Pro Asn Asn Val Cys
145                 150                 155                 160

Thr Gly Val Leu Thr Arg Arg Gly Gly Ile Cys Asn Gly Asp Gly Gly
                165                 170                 175

Thr Pro Leu Val Cys Glu Gly Leu Ala His Gly Val Ala Ser Phe Ser
            180                 185                 190

Leu Gly Pro Cys Gly Arg Gly Pro Asp Phe Phe Thr Arg Val Ala Leu
        195                 200                 205

Phe Arg Asp Trp Ile Asp Gly Val Leu Asn Asn Pro Gly Pro
    210                 215                 220
```